United States Patent [19]

Oh

[11] Patent Number: 4,770,661
[45] Date of Patent: Sep. 13, 1988

[54] CONVERSION FEMORAL ENDOPROSTHESIS

[76] Inventor: Indong Oh, 851 Lyndon St., South Pasadena, Calif. 91030

[21] Appl. No.: 340,027

[22] Filed: Jan. 18, 1982

[51] Int. Cl.⁴ .............................................. A61F 2/32
[52] U.S. Cl. ...................................... 623/23; 623/18; 623/22
[58] Field of Search .................. 3/1.912, 1.913, 1.911; 128/92 C, 92 CA

[56] References Cited

U.S. PATENT DOCUMENTS

| | | | |
|---|---|---|---|
| 3,843,975 | 10/1974 | Tronzo | 128/92 CA X |
| 4,004,300 | 1/1977 | English | 3/1.913 |
| 4,021,865 | 5/1977 | Charnley | 3/1.913 |
| 4,172,296 | 10/1979 | D'Errico | 3/1.912 |
| 4,199,824 | 4/1980 | Niederer | 3/1.913 |

FOREIGN PATENT DOCUMENTS 2839661 9/1979 Fed. Rep. of Germany ....... 3/1.912

Primary Examiner—Richard J. Apley
Assistant Examiner—David J. Isabella
Attorney, Agent, or Firm—Gordon L. Peterson

[57] ABSTRACT

A hip-joint prosthesis which provides for universal motion about three transverse pivot axes comprising a femoral member adapted to be coupled to the femur and a cup assembly partially receiving the femoral member. The cup assembly is slidably received in the acetabulum. Motion about one of the pivot axes can occur in the prosthesis and motion about the other two pivot axes is forced to occur between the cup assembly and the acetabulum.

6 Claims, 2 Drawing Sheets

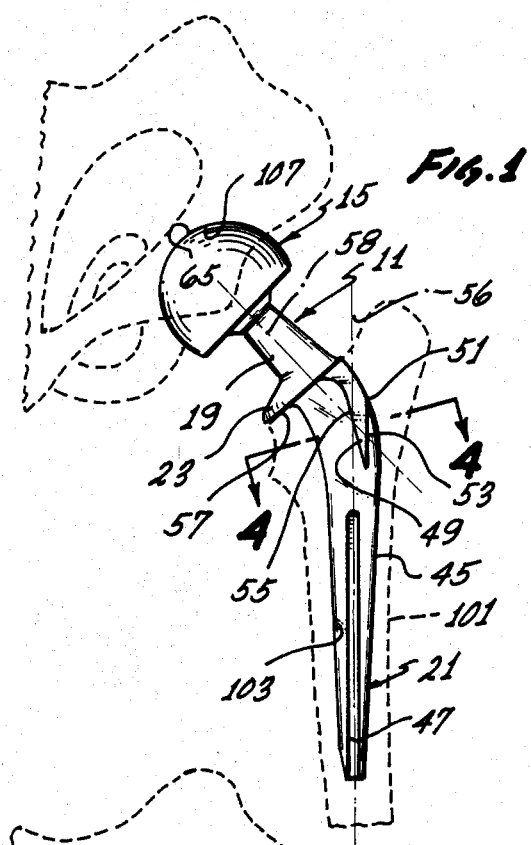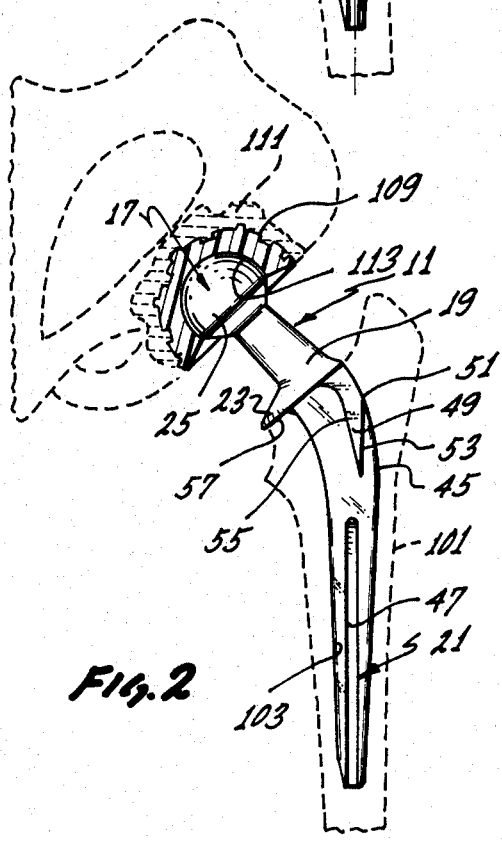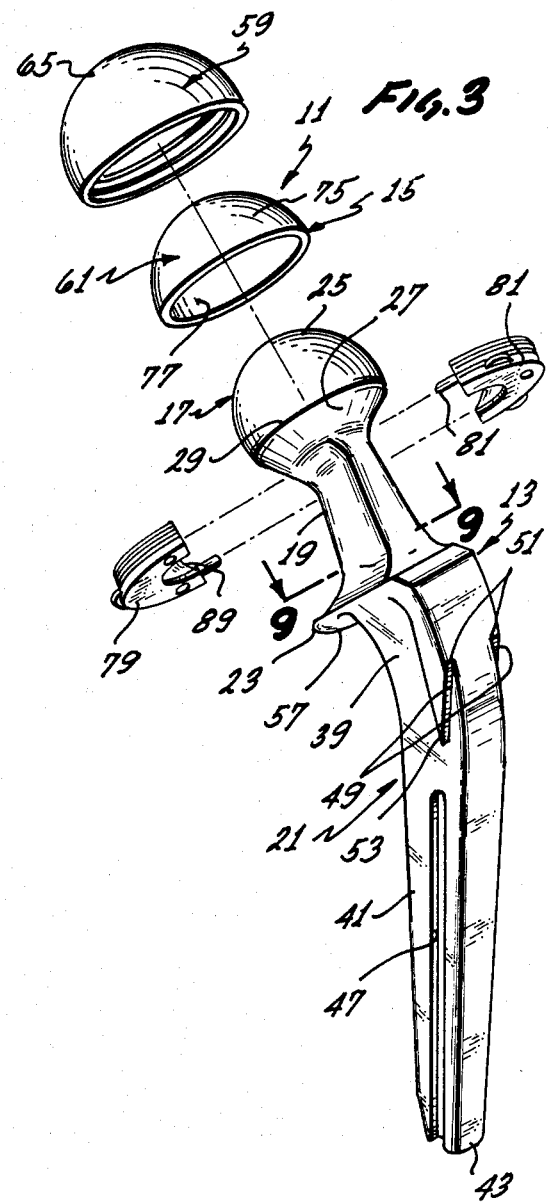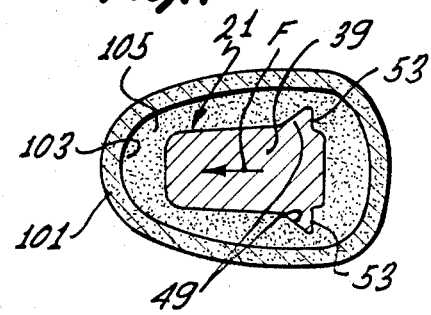

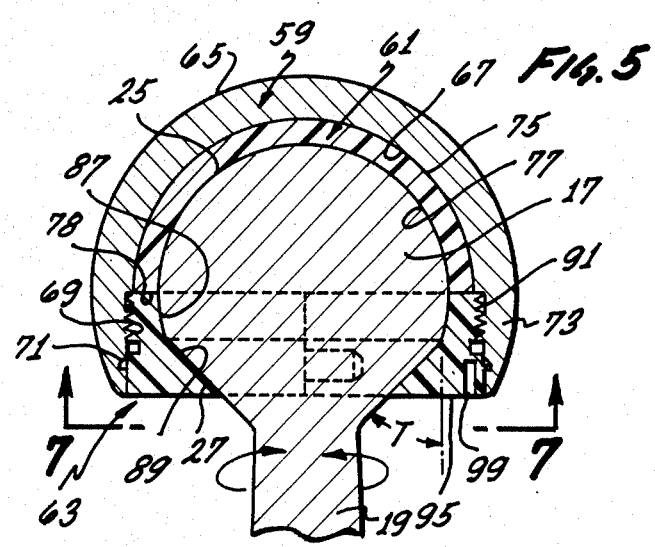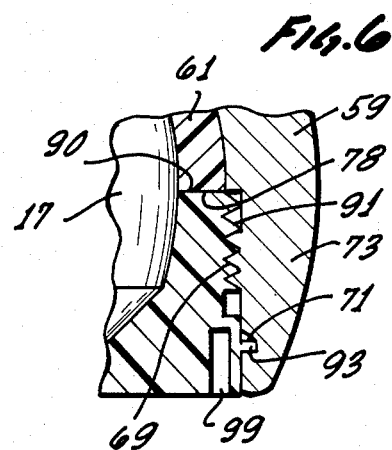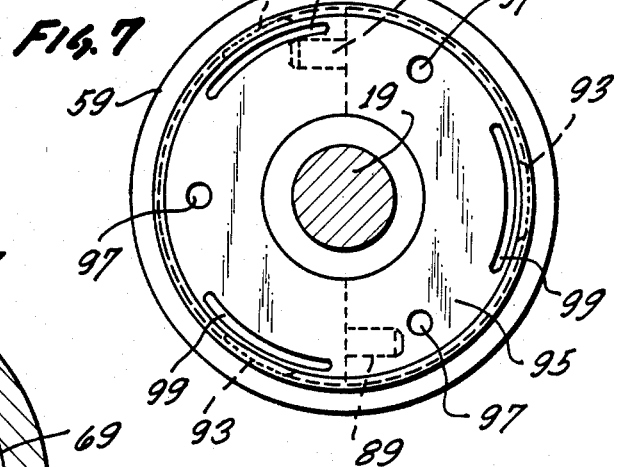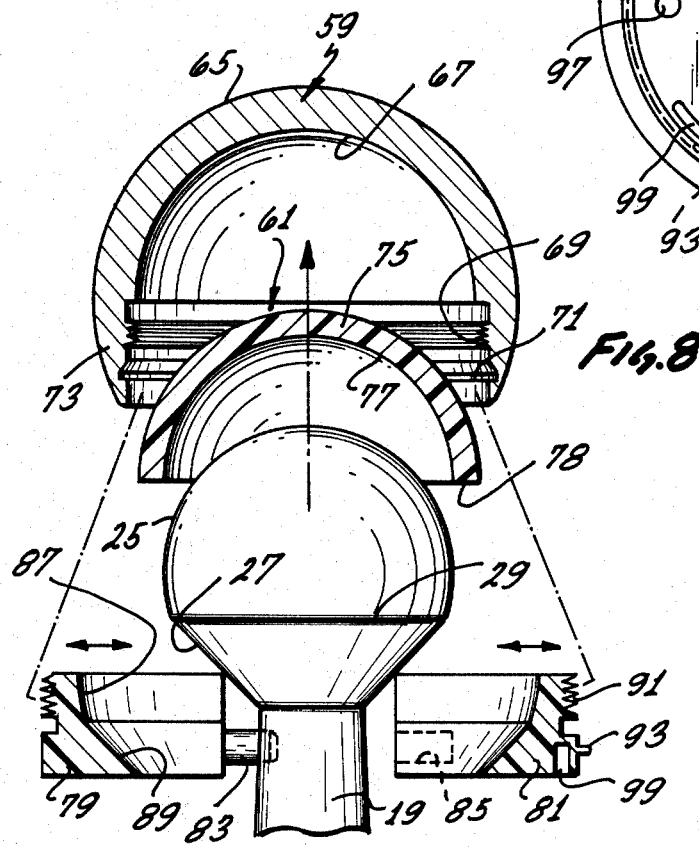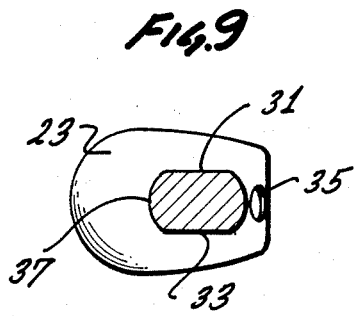

CONVERSION FEMORAL ENCOPROSTHESIS

BACKGROUND OF THE INVENTION

The joints of a human skeletal structure typically comprise a ball and a socket. Joints, such as the hip and shoulder, provide for universal motion, i.e., relative motion about three transverse pivot axes.

For example, a hip joint includes a femoral head which is joined to the proximal femur by a neck which is angularly disposed relative to the axis of the femur and relative to the vertical axis of the human body. A natural socket or acetabulum receives the femoral head and cooperates therewith to form a universal joint which permits relative motion about three transverse pivot axes.

Various progressive diseases, such as osteoarthritis can bring about deterioration of the natural socket and/or the natural femoral head. When this occurs, the diseased component can be replaced or rebuilt using an appropriate prosthetic device. For example, in total surface replacement, an acetabular cup is cemented into the natural socket or acetabulum, and a femoral cup is cemented over the natural femoral head after reaming. The femoral cup fits into the acetabular cup to provide the necessary universal motion.

In total hip replacement, an acetabular cup is cemented into the acetabulum, and the natural femoral head and neck are removed. A femoral member comprising an elongated stem, a neck and a head is mounted within the proximal femur by cementing of the stem into the femur. The head is received in the cup to provide the desired universal motion. One example of this construction is shown in Chambers U.S. Pat. No. 3,656,184.

In another form of total hip replacement, a femoral cup is mounted on the head of the prosthetic femoral member. The femoral cup is received within the acetabulum. Constructions of this type are shown by way of example in the following U.S. patents:

Giliberty U.S. Pat. No. 3,813,699
D'Errico U.S. Pat. No. 4,172,296
Khovaylo U.S. Pat. No. 4,214,463

In each of these constructions, the head is mounted within the femoral cup for universal movement, and similarly, the femoral cup is mounted for universal movement within the acetabulum. Accordingly, as the hip joint is used, the motion may be accommodated by either or both of these interfaces to the extent allowed by the ratio of the head-to-neck diameters and the overlap of the femoral cup past the equator of the femoral head.

Unfortunately, in use of this latter system, a pseudocapsule may form and impede the movement of the femoral cup in the acetabulum. In this event, motion occurs primarily or entirely between the head and the femoral cup, and this can accelerate deterioration of the cartilage by uneven lubrication between the femoral cup and the natural acetabulum and the creation of local stresses in the natural acetabulum due to the lack of relative movement between the femoral cup and the natural acetabulum. Thus, leaving to chance the interface which accommodates the hip motion may accelerate the deterioration of the joint.

The stem of the femoral member may include flanges or fins extending along the lateral, i.e., outer proximal edge of the stem. The fins increase the strength of the femoral member and enhance bonding of the stem within the intermedullary canal of the femur. For example, fins of this type are shown in Charnley U.S. Pat. No. 4,021,865. As disease progressively worsens, it may become necessary to replace the femoral member. Unfortunately, the fins of the prior art make the femoral member difficult to remove from the femur due to the location and curvature of the fins.

SUMMARY OF THE INVENTION

This invention provides a femoral endoprosthesis conversion in which some of the universal motion of the joint is forced to occur in the natural socket. This is accomplished by providing a prosthesis which accommodates only some of the motion of the joint. Accordingly, joint motion is shared between two bearing surfaces, one of which is along the natural socket and the other of which is within the prosthesis. Because motion is forced to occur in the natural socket, the femoral component does not become locked in the natural socket and much more even lubrication of the natural socket occurs. In addition, to the extent that the motion is accommodated by the prosthesis, wear on the natural socket is reduced. Although this invention is described with respect to a hip joint, its features are equally applicable to other joints, such as a shoulder joint, which must accommodate universal motion.

Universal motion may be considered as motion about three transverse axes. With this invention, motion in the natural socket is forced to occur by permitting the prosthesis to accommodate motion about no more than two of the three transverse axes. Accordingly, motion about at least a third of the axes is forced to occur between the prosthesis and the natural socket.

It is preferred to have most of the universal motion occur in the natural socket. Accordingly, the prosthesis preferably provides for motion about only one of the three transverse axes. More particularly, the prosthesis can conveniently accommodate motion about an axis extending generally along or parallel to the axis of the neck of the prosthesis.

In a preferred construction, the prosthesis includes a head adapted to be coupled to a bone and a cup assembly at least partially receiving the head and having an exterior surface. At least a portion of the exterior surface of the cup assembly is generally spherical and adapted to be slidably received in a natural socket of a joint. Means is provided for mounting the head within the cup assembly for motion relative to the exterior surface of the cup assembly about at least one axis and not more than two axes. Accordingly, motion about at least a third of the axes is forced to occur between the exterior surface of the cup assembly and the natural socket.

Another advantage of this construction is that the femoral component need not be removed as the disease progressively deteriorates the natural socket. In this event, an acetabular cup is cemented in the natural socket, and the cup assembly of the prosthesis is removed to allow the head to be received in the acetabular cup. Thus, this invention provides for ease of accommodating the progressive nature of the disease.

To enable the head to be used subsequently in association with the acetabular cup, the head preferably has a generally spherical surface. The spherical surface of the head can be constrained to rotate about only one of the axes in various different ways. Preferably, mating generally conical surfaces are provided on the head and the cup assembly so that the motion about such axis occurs along the conical surfaces.

In a preferred construction, the cup assembly includes a cup, an insert or bearing within the cup and a locking ring at least partly within the cup. The bearing has a spherical surface which mates with the spherical surface of the head, and the locking ring has a conical surface that mates with the conical surface of the head. The cup assembly can be held together by fastener means, such as screw threads on the locking ring and the cup, and means such as a cooperating tab and recess is provided for preventing loosening of the locking ring. The locking ring preferably has an exposed portion and means on such exposed portion for cooperating with a wrench to facilitate relative rotation of the cup and the locking ring for operating the threads.

The head may form a portion of a femoral member or component which also includes a neck and an elongated stem. The stem has a curved portion and a generally linear portion, with the linear portion terminating in a distal end. The stem also has a lateral edge which is curved along the curved portion of the stem. The stem is cemented within the intermedullary canal of the femur.

First and second fins are provided on the stem and they extend distally along the lateral edge of the curved portion of the stem from a location adjacent the neck to an intermediate location along the curved portion of the stem. However, to facilitate removal of the femoral member from the femur, each of the fins has a lateral surface region which extends distally of the intermediate location to a distal end and which is generally parallel to the axis of the linear portion of the stem. Each of the lateral surface regions lies medially, i.e., inwardly, of the lateral edge of the stem, and the distal end portion of each of the fins is tapered as viewed in a frontal plane and, if desired, as viewed in a lateral plane.

Because of the configuration of the lateral surface regions as described above, the femoral member can be withdrawn from the femur with greater ease than if the fins had a configuration which would impede such removal. Preferably, the fins and the curved portion of the stem both decrease in width as they extend medially. This forms a tapered configuration which resists one of the major forces most commonly applied to this region of the prosthesis during use.

To increase the strength of the bond between the femoral member and the cement, the stem may have one or more grooves on the linear portion of the stem. To facilitate removal of the femoral member, the grooves preferably extend axially of the linear portion of the stem.

In a preferred construction, the neck is of circulo-trapezoidal shape as viewed in radial cross section. This allows a relatively high head-to-neck diameter ratio in both the sagittal and frontal planes and, consequently, an increased range of motion.

The invention, together with additional features and advantages thereof, may best be understood by reference to the following description taken in connection with the accompanying illustrative drawing.

BRIEF DESCRIPTION OF THE DRAWING

FIG. 1 is a frontal elevational view showing in full lines a femoral endoprosthesis conversion constructed in accordance with the teachings of this invention and in dashed lines a portion of the natural-pelvis, acetabulum and femur.

FIG. 2 is a frontal elevational view similar to FIG. 1 with the cup assembly of the prosthesis removed and with an acetabular cup cemented into the acetabulum.

FIG. 3 is an exploded perspective view of the prosthesis.

FIG. 4 is an enlarged sectional view taken generally along line 4—4 of FIG. 1.

FIG. 5 is a fragmentary axial sectional view taken on an axial plane through the cup assembly, head and a portion of the neck of the prosthesis.

FIG. 6 is an enlarged, fragmentary, sectional view illustrating the joint between the locking ring and the femoral cup.

FIG. 7 is a sectional view taken generally along line 7—7 of FIG. 5.

FIG. 8 is an exploded sectional view of the cup assembly and a portion of the head and neck.

FIG. 9 is a sectional view taken generally along line 9—9 of FIG. 3.

DESCRIPTION OF THE PREFERRED EMBODIMENT

FIGS. 1–3 show a hip joint prosthesis 11 in the form of a femoral endoprosthesis conversion. The prosthesis 11 includes a femoral member or component 13 and a femoral cup assembly 15.

The femoral member 13 is preferably integrally constructed from a biocompatible metal, such as ultra high strength, cold worked and aged, wrought cobalt chromium nickle alloy. This alloy is preferred because it has high fatigue strength. Generally, the femoral member 13 is configured similarly to the proximal femur.

The femoral member 13 comprises a head 17, a neck 19, a stem 21 joined to the head by the neck, and a collar 23 around the neck near its juncture with the stem. As shown in FIGS. 3, 5 and 8, the head 17 has a spherical surface 25 and a conical surface 27 which intersects the spherical surface along a circular line 29. In the embodiment illustrated, the spherical surface 25 extends for over 180 degrees, and the axis of the conical surface 27 passes through the center of the spherical surface 25. The surfaces 25 and 27 are smooth and polished, and the major diameter of the conical surface 27 is substantially equal to the diameter of the circular line 29. The conical surface 27 has an angle of taper t (FIG. 5) which may be, for example, 50 degrees.

The neck 19 has an axis which is coaxial with the axis of the conical surface 27 and which passes through the center of the spherical surface 25. The neck extends generally linearly. Although the neck 19 may have different cross-sectional configurations, a circulo-trapezoidal configuration of the type shown in FIG. 9 is preferred. This configuration includes generally planar frontal and posterior surfaces 31 and 33, respectively, joined by curved lateral and medial surfaces 35 and 37, respectively. The surfaces 31 and 33 are longer than the surfaces 35 and 37 and they taper slightly toward each other as they extend toward the medial surface 37 to provide a somewhat trapezoidal configuration. Unlike a neck of circular cross-section, the circulo-trapezoidal shape enables the surgeon to easily ascertain the orientation of the stem 21 and it provides an increased range of motion due to relatively high head-to-neck diameter ratios which may be, for example, 1:2.14 in the frontal plane, i.e., as viewed in FIGS. 1 and 2, and 1:3.52 in the sagittal plane, i.e., side elevation.

The stem 21 is elongated and has a curved portion 39 and a generally linear portion 41 which terminates in a distal end 43. The stem 21 has a lateral edge 45 (FIG. 1) which is curved along the curved portion of the stem. The linear portion 41 has identical elongated grooves 47 (only one being shown in FIGS. 1-3) extending axially thereof from a location adjacent the curved portion 39 to the distal end 43. It is preferred to fillet and round the corners of the grooves and stem to reduce stress risers in the cement when the prosthesis is implanted.

Identical fins 49 (FIGS. 1-4) extend distally along the lateral edge 45 of the curved portion 39 from a location contiguous the neck 19 to an intermediate location 51 and to a distal end. The lateral surface regions 53 are generally parallel to the axis of the linear portion 41 of the stem 21, and each of the lateral surface regions lies medially of the lateral edge 45 of the stem. In the embodiment illustrated, the lateral surface regions 53 are generally planar. As shown in FIG. 4, the fins 49 and the curved portion 39 of the stem 21 are of decreasing width as they extend medially and each of the fins is generally triangular in cross-section. As shown in FIGS. 1-3, the distal end portion of each of the fins 49 preferably tapers to a point as viewed in frontal and lateral planes. Thus, each of the fins 49 has a medial edge 55 which is inclined toward the lateral surface region 53 as it extends distally as shown in FIGS. 1-3.

The curved portion 39 causes the axis of the neck 19 to extend at an angle with respect to the axis 56 (FIG. 1) of the linear portion 41 of the stem 21. By way of example, the axis 58 (FIG. 1) of the neck 19 may be inclined about 46 degrees relative to the axis 56 of the linear portion 41 of the stem 21.

In the embodiment illustrated, the collar 23 is of rounded configuration as shown in FIG. 9. Although the collar may be of different configurations and extend at different angles, in the embodiment illustrated, the collar has a lower surface 57 which forms an included angle with the axis 56 of the linear portion 41 of approximately 50 degrees. This angle facilitates the surgery without encroaching into an area of the greater trochanter.

The cup assembly 15 includes a femoral cup 59, an inner shell or bearing 61 and a locking ring 63 (FIGS. 3, 5 and 8). The cup 59 is preferably constructed of a biocompatible metal and has a smooth spherical exterior surface 65, a spherical inner surface 67 concentric with the surfaces 65, internal threads 69 immediately outwardly of the spherical inner surface 67, and an annular locking groove 71. The spherical exterior surface 65 extends for well over 180 degrees, and the spherical inner surface 67, in the embodiment illustrated, extends for about 180 degrees. Thus, the cup 59 may be considered as a hemispherical shell having an integral skirt 73. The skirt has a spherical exterior surface and has the threads 69 and the locking groove 71 on its inner surface.

The shell 61 is in the form of a hemispherical shell having a hemispherical exterior surface 75 and a hemispherical interior surface 77 which mate with the surface 67 and the spherical surface 25 of the head 17, respectively. The shell 61 terminates in an annular edge 78. The shell 61 is preferably constructed of a biocompatible plastic, such as polyethylene, and serves a bearing function.

The locking ring 63 preferably comprises locking ring segments which may be in the form of half sections 79 and 81 as shown in FIGS. 3 and 8. Each of the half sections 79 and 81 includes a projection 83 and a mating recess 85 for receiving the projection of the other half section to thereby permit assembly of the half sections into the locking ring 63. Each of the half sections 79 and 81 is preferably constructed of a biocompatible plastic material, such as polyethylene. The half sections 79 and 81 facilitate assembly of the locking ring onto the femoral member 13.

The locking ring 63 has an interior spherical surface 87 (FIG. 8) and an interior conical surface 89 which mate with the spherical surface 25 and the conical surface 27 of the head 17, respectively. Thus, the conical surface 89 has an axis which passes through the center of the spherical surface 87, and these two surfaces intersect to form a circle. The locking ring 63 has an inner annular surface 90 and external threads 91 which can be threaded into the internal threads 69 of the cup 59. The locking ring 63 also has three radially extending flanges or tabs 93 which are received in the locking groove 71 for preventing the locking ring 63 from loosening in the cup 59.

The locking ring 63 has an exposed planar surface 95 (FIG. 7) which faces generally toward the collar 23. The surface 95 has recesses 97 for receiving prongs of a wrench (not shown) to facilitate screwing the locking ring 63 into and out of the cup 59. A set of elongated, circumferentially extending recesses 99 may also be provided in the surface 95 to facilitate the radial inward deflection of the outer peripheral region of the locking ring. The recesses 99 are radially inwardly of the tabs 93, respectively, and this facilitates forcing of the tabs 93 into the groove 71. Of course, other means for drivingly coupling a tool to the locking ring 63 could be used.

In the assembled condition shown in FIG. 5, the shell 61 fits within the cup 59 and is held in a fixed position relative to the cup 59 by the locking ring 63 as a result of the inner surface 90 of the locking ring bearing against an annular edge 78 of the shell. All of the spherical surfaces of the cup assembly 15 and the head 17 are concentric, and the conical surfaces 27 and 89 are coaxial. The interior spherical surface 87 of the locking ring 63 forms an extension of the interior spherical surface 77 of the shell 61, and but for the conical surfaces 27 and 89, would cooperate with the spherical surface 25 of the head 17 to allow universal motion of the head within the cup assembly 15. However, the conical surfaces 27 and 89 cooperate to permit rotational movement of the head 17 relative to the cup assembly 15 only about the axis of the conical surfaces. Although the coincident axes of the conical surfaces 27 and 89 could extend in different directions, in the embodiment illustrated, they are coaxial with the neck 19.

FIGS. 1 and 2 show how the prosthesis 11 can be used. In FIG. 1, the stem 21 is installed in a femur 101 utilizing known surgical procedures. Generally, the stem 21 is retained in the intermedullary canal 103 (FIGS. 1 and 4) of the femur by a suitable cement 105, and the collar 23 rests on the upper surface of the femur 101. The cup assembly 15 is slidably received in the natural hip socket or acetabulum 107.

In use, the joint formed by the acetabulum 107 and the prosthesis 11 must accommodate universal motion, i.e., motion about three transverse pivot axes. The head 17 slides within the locking ring 63 and the shell 61 is allowed by the conical surfaces 27 and 89 to provide pivotal motion about the axis 58 of the neck 19. Because this is the only pivotal motion that can be accommodated by the prosthesis 11, all other pivotal motion must occur as a result of sliding contact between the acetabulum 107 and the spherical exterior surface 65 of the cup assembly 15. In other words, motion about the other two transverse pivotal axes must occur as a result of this sliding motion within the acetabulum 107. This sliding movement in the acetabulum 107 reduces the likelihood that the femoral member will freeze in the acetabulum and is intended to promote lubrication of the acetabulum.

If the disease progresses, it may eventually be necessary to provide an acetabular cup 109 in the acetabulum as shown by way of example in FIG. 2. The acetabular cup 109 is fixedly mounted in the acetabulum utilizing cement 111 using conventional surgical techniques. The acetabular cup 109 is not, per se, a part of this invention, and it can be of any suitable design. However, the cup 109 should have an interior spherical surface 113 adapted to slidably mate with the spherical surface 25 of the head 17.

Thus, as the disease progressively deteriorates the acetabulum 107, the cup 109 is installed, and the cup assembly 15 is removed from the femoral member 13 to expose the head 17. The head 17 is inserted into the interior spherical surface 113 so that thereafter universal motion is provided for by sliding contact of the spherical surfaces 25 and 113. All of this can be done without removing the femoral member 13 from the femur 101. Thus, the next stage in treating the progressive disease can be accomplished without removing of the femoral member 115.

In use of the prosthesis 11, there is a major force acting in the direction of the arrow F in FIG. 4. The sloping surfaces on the fins 49 and on the stem 21 as shown in FIG. 4 cooperate with the cement 105 to create a wedge-like effect which strongly resists the force F. If it should become necessary to remove the femoral member 13 from the femur, the lateral surface regions 53 of the fins, being parallel to the axis of the linear portion 41 of the stem 21, do not impede such withdrawal to the extent that they would if this relationship were not present. Also, the tapered nature of the fins 49 as viewed in the frontal plane further reduces the resistance to surgical removal of the femoral member 13. Because the grooves 47 extend axially, they also tend to facilitate the surgical removal of the femoral member 13.

Although an exemplary embodiment of the invention has been shown and described, many changes, modifications and substitutions may be made by one having ordinary skill in the art without necessarily departing from the spirit and scope of this invention.

I claim:

1. A prosthesis comprising:
a head having an exterior surface, at least a portion of said exterior surface being generally spherical;
means coupled to said head for use in attaching the head to a bone whereby the head moves with the bone when the head is attached to the bone;
a cup assembly having an exterior surface, at least a portion of said exterior surface being generally spherical and adapted to be slidably received in a natural socket of a joint, said cup assembly having an interior cavity for at least partially receiving said head;
said cup assembly and said head including means for mounting the head within the interior cavity of the cup assembly for motion relative to the exterior surface of the cup assembly about at least one pivot axis but about fewer pivot axes than is required for universal movement of the bone relative to the natural socket whereby at least some sliding movement between the exterior surface of the cup assembly and the natural socket is forced to occur in order to obtain relative universal movement between the bone and the natural socket;
said attaching means including a stem and a neck joining said head to said stem to form a femoral member; and
said stem having a lateral edge, a curved portion and a generally linear portion with the linear portion terminating in a distal end, and including at least one fin receivable in the intermedullary canal and cooperable with cement in said canal, said fin being contiguous the stem along its length and having a lateral surface region which extends distally and generally parallel to the axis of the linear portion of the stem, said lateral surface region lying medially of the adjacent portion of the lateral edge.

2. A prosthesis comprising:
a head having an exterior surface, at least a portion of said exterior surface being generally spherical;
means coupled to said head for use in attaching the head to a bone whereby the head moves with the bone when the head is attached to the bone;
a cup assembly having an exterior surface, at least a portion of said exterior surface being generally spherical and adapted to be slidably received in a natural socket of a joint, said cup assembly having an interior cavity for at least partially receiving said head;
said cup assembly and said head including means for mounting the head within the interior cavity of the cup assembly for motion relative to the exterior surface of the cup assembly about at least one pivot axis but about fewer pivot axes than is required for universal movement of the bone relative to the natural socket whereby at least some sliding movement between the exterior surface of the cup assembly and the natural socket is forced to occur in order to obtain relative universal movement between the bone and the natural socket;
said attaching means including a stem and a neck joining said head to said stem to form a femoral member; and
the stem having a curved portion, a generally linear portion with the linear portion terminating in a distal end, and a lateral edge which is curved along the curved portion of the stem, first and second fins extending distally along the lateral edge of the curved portion of the stem from a location adjacent the neck to an intermediate location along the curved portion of the stem, each of said fins having a lateral surface region which extends distally of said intermediate location to a distal end and which is generally parallel to the axis of the linear portion of the stem, each of said lateral surface regions lying medially of the adjacent portion of said lateral edge of the stem, and a portion of each of the fins adjacent the distal end thereof tapering toward such distal end of the associated fin as viewed in a frontal plane.

3. A prosthesis as defined in claim 2 wherein each of said fins is of decreasing width as it extends medially.

4. A prosthesis as defined in claim 2 wherein said curved portion of said stem is of decreasing width as it extends medially.

5. A prosthesis as defined in claim 2 wherein said linear portion of said stem has at least one groove extending generally axially thereof.

6. A prosthesis as defined in claim 2 wherein the neck is of circulo-trapezoidal configuration in axial cross section.

* * * * *